United States Patent [19]

Smeyers et al.

[11] Patent Number: 5,440,391
[45] Date of Patent: Aug. 8, 1995

[54] METHOD AND DEVICE FOR DETERMINING A POSITION OF AT LEAST ONE LEAD OF AN ELECTRONIC COMPONENT

[75] Inventors: Gust Smeyers, Meise; Luc Vanderheydt, Wilsele, both of Belgium

[73] Assignee: ICOS Vision Systems n.v., Belgium

[21] Appl. No.: 777,366

[22] PCT Filed: Mar. 22, 1991

[86] PCT No.: PCT/BE91/00023

§ 371 Date: Nov. 22, 1991

§ 102(e) Date: Nov. 22, 1991

[87] PCT Pub. No.: WO91/15104

PCT Pub. Date: Oct. 3, 1991

[30] Foreign Application Priority Data

Mar. 23, 1990 [BE] Belgium ............................ 09000331

[51] Int. Cl.6 ............................................. G01N 21/88
[52] U.S. Cl. ................................... 356/375; 356/237
[58] Field of Search ............... 356/375, 376, 394, 237, 356/372, 383, 384; 250/560, 561, 562, 221; 358/106, 107; 382/8, 58; 348/87, 92, 94, 95, 126

[56] References Cited

U.S. PATENT DOCUMENTS

| 4,435,837 | 3/1984 | Abernathy | 356/375 |
|---|---|---|---|
| 4,507,557 | 3/1985 | Tsikos | 356/375 |
| 4,582,430 | 4/1986 | Price | 356/375 |
| 4,710,620 | 12/1987 | Kunkel | 356/375 |
| 4,728,195 | 3/1988 | Silver | 356/394 |
| 4,777,360 | 10/1988 | Carner, Jr. | 356/375 |
| 4,873,651 | 10/1989 | Raviv | 356/375 |
| 5,008,555 | 4/1991 | Mundy | 356/376 |
| 5,013,927 | 5/1991 | Tsikos et al. | 356/376 |

*Primary Examiner*—Hoa Q. Pham
*Attorney, Agent, or Firm*—Wood, Phillips, VanSanten, Clark & Mortimer

[57] ABSTRACT

Method and device for determining a position with respect to a reference plane of at least one lead of an electronic component, wherein said lead is illuminated from a first and respectively second position situated sideways and out of the plane wherein the electronic component is disposed and wherein a first and respectively a second shadow image is formed of at least a part of said lead on an image plane, which second position is different from said first position and wherein said first and respectively said second shadow image is located and a third and respectively a fourth position is determined to this end and said position is determined from said third and fourth position.

16 Claims, 2 Drawing Sheets

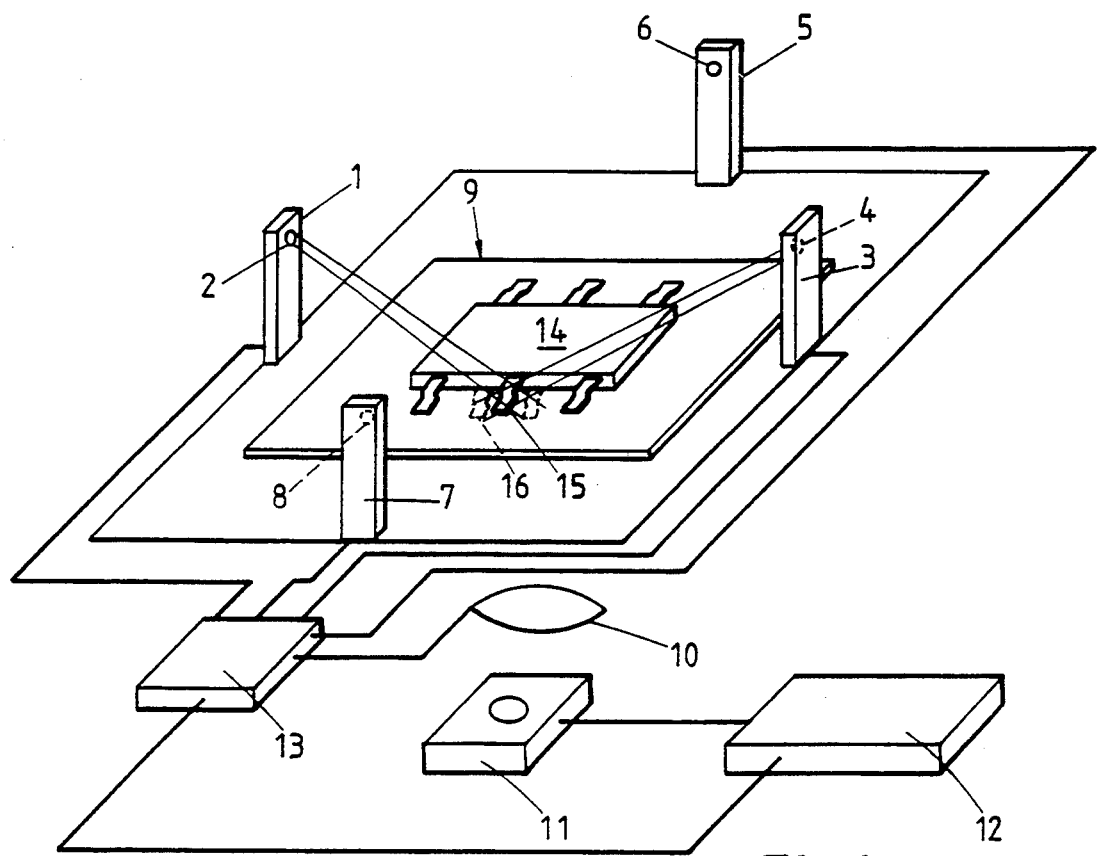
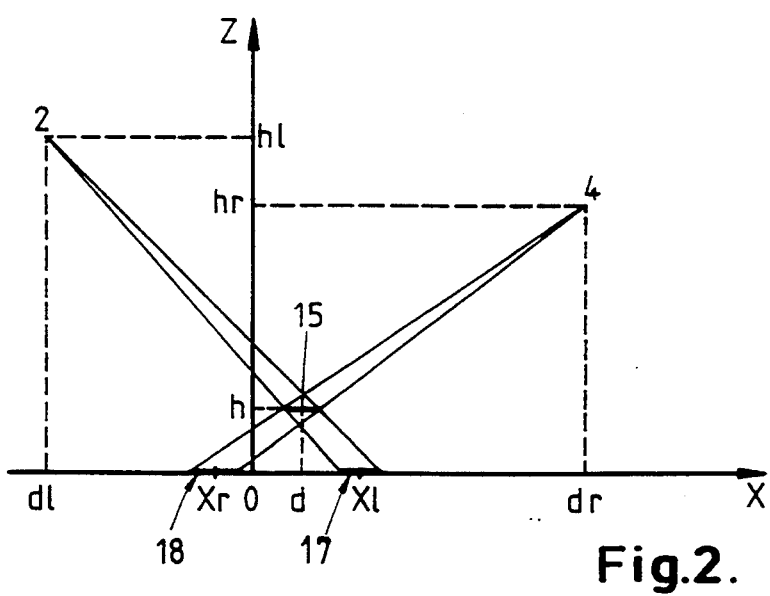
Fig.1.
Fig.2.

METHOD AND DEVICE FOR DETERMINING A POSITION OF AT LEAST ONE LEAD OF AN ELECTRONIC COMPONENT

FIELD OF THE INVENTION

The present invention relates to a method for determining a position of at least one lead of an electronic component, especially a semi-conductor element, with respect to a reference plane, wherein said lead is illuminated from a first position situated sideways and out of a plane defined by the electronic component, and wherein a first image of at least a part of said lead is formed on an image plane. The invention also relates to a device for performing the method.

BACKGROUND OF THE INVENTION

Such a method is used for determining the mutual position differences between leads of an electronic component, in particular a semi-conductor element. There are several reasons for which the leads of an electronic component are not always aligned accurately. However, for the assembling of a chip on a card it is important that the leads are positioned well with respect to the soldering areas. A deviation between a lead and a soldering area can end in that there is no mechanical contact between soldering area and lead and therefore that no electronic contact will be realised so that the whole card can become useless. However, since the leads are frequently bent with respect to the desired distance, it is necessary to verify to which extend this bending can lead to an inoperational card. The known method allows to check, by a position determination whether the leads are arranged correctly. To this end, a two-dimensional image is generated from the underside of the electronic component for example by means of a television camera. The image is realized by the fact that the electronic component is illuminated by a coherent light beam which is arranged at a certain angle with respect to the camera. The position in the image of the light source reflected on the lead comprises the necessary information to deduce herefrom the position of the lead.

A drawback of the known method and of the device used therein is the necessity to use a coherent light beam for giving the beam reflected on the lead a sufficient intensity in order to form a clear image. The latter requires the use of a laser as a light source, which involves on the other hand that the device has to be covered adequately, which renders in its turn the used device and method expensive.

SUMMARY OF THE INVENTION

An object of the present invention is to realise a method and a device for determining a position of at least one lead of an electronic component, wherein use is made of simpler and therefore cheaper means without influencing the reliability of the measurement negatively.

To this end, a method according to the invention is characterized in that a shadow image is formed when forming said first image and said lead is illuminated from a second position different from said first position for forming a second shadow image on said image plane, and said first and respectively second shadow image is located and a third respectively fourth position is determined to this end and in that said position is determined from said third and fourth position. Due to the use of shadow images, it is not necessary to use a coherent light source, such as a lazer, and it is therefore also not necessary to cover the device against light of a too high intensity. By determining further two shadow images it is possible to establish unambiguously the position of the lead. Indeed, each deviation from a standard position automatically results in that both shadow images will be located in a position different from the position of the standard images, so that the position of the lead can always be determined unambiguously and reliably from the position of the set of shadow images.

A first preferred embodiment of a method according to the invention is characterized in that said third and respectively fourth position is located substantially in the middle of said first and respectively second shadow image. Due to this, the third and fourth position is simply to locate.

Advantageously, illuminating from said first and second position is done from substantially opposite positions. Due to this, the shadow images are situated according to the same axis which simplifies the position determination.

A device according to the invention is characterized in that illumination means are further provided for illuminating said lead from a second position different from said first position and said image formation member is further provided for forming a second shadow image of at least a part of said lead illuminated from said second position, which device comprises a position determining member connected to said image formation member and provided for locating said first and respectively second shadow image and for determining to this end a third and respectively fourth position as well as for determining said position from said third and fourth position.

A first preferred embodiment of a device according to the invention is characterized in that said position determining means are provided for determining said position from the difference between said third and fourth position. Because of this, the determination of said position can be carried out easily and quickly.

A second preferred embodiment of a device according to the invention is characterized in that said device comprises a frosted-glass plate disposed in the beam path between said lead and said image formation member. A frosted-glass plate allows to form a clear shadow image.

BRIEF DESCRIPTION OF THE INVENTION

The invention will now be described into more details on the basis of an embodiment shown in the drawings. In the drawings:

FIG. 1 shows schematically an embodiment of a device according to the invention;

FIG. 2 shows the formation of the first and second shadow image;

In the drawings, the same or an analogous element has the same reference numeral.

DETAILED DESCRIPTION OF THE INVENTION

Figure 3:
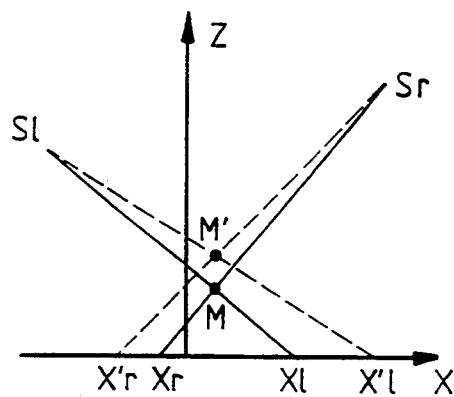
FIG. 3 shows the image formation for two different positions of a lead in a direction perpendicular to the projection plane.

The embodiment of a device according to the invention represented schematically in FIG. 1 comprises four holders 1, 3, 5 and 7 comprising each a light source 2, 4, 6 and 8. The light emitted by each light source falls aslant upon one or more leads 15 of an electronic component 14, in particular a semi-conductor element. The electronic component is disposed on or right above a frosted plate 9 which is a component of an image formation member. Since the light is reflected, a shadow will be formed on and behind the frosted-glass plate each time near one of the illuminated leads. By using a frosted-glass plate, a shadow image of the lead or leads is obtained at the level of an image plane arranged behind the frosted-glass plate. This image plane is formed for example by a projection plane on which the light passing through the frosted-glass plate is projected. The image formation member further comprises a lens system 10 and a camera 11, for example a CCD camera. The camera 11 is connected with a data processing system 12 which takes care of the camera control as well as of the processing of the data recorded by the camera. The data processing system is further connected with an interface 13 which is further connected with the light sources 2, 4, 6 and 8 in order to control in this way switching the light sources on and off.

The oblique angle at which the emitted light falls in is preferably equal to 45°, which is advantageous for forming shadow images having sharp contours which can be located and positioned clearly and unambiguously. Moreover, for an angle of 45° a displacement in the z-direction is equal to the displacement in the x-direction. However, it will be clear that besides 45° other values are also possible. A combination of one light beam falling in under a 90° angle and the other light beam under an angle of 0° is to be excluded since this combination does not provide any useful information.

It will be clear that the embodiment shown schematically in FIG. 1 only relates to one possible embodiment and that several alternative embodiments are possible. Thus, it is for example possible to use as the illumination means not four but only two lamps which are arranged substantially opposite to one another, such as the lamps 2 and 4 for example, and which illuminate the leads of the electronic component preferably under an oblique angle. Moreover, the lamps must not necessarily be disposed at the same height and may be shifted as well in height (z-direction) as in the y-direction with respect to one another. Disposing them on a corresponding y-position does simplify the determination of the position of the considered lead based on the position of the shadow images.

In a further embodiment use is made of only one light source which is mounted on a movable arm. In this way, the light source can be placed into different positions and it can illuminate from each of these different positions the leads of an electronic component. This movable arm can be controlled for example by the data processing unit 12.

It is, however, important that the light sources are arranged sideways with respect to the electronic component and out of the plane wherein the electronic component is disposed, otherwise no useful shadow images will be formed.

Preferably, the electronic component is suspended somewhat above the frosted-glass plate 9 having its lead directed towards the plate. This prevents the leads from being damaged or bent. The electronic component is kept in said position for example by means of a grab or a sucker which is also appropriate for bringing each time a next component in that position wherein the measurement takes place. However, it will be clear that when acting carefully, the electronic component can be laid on the frosted-glass plate itself.

Instead of using a frosted-glass plate, it is of course also possible to use a coated glass plate. Of course, the camera 11 can be replaced by another image formation means such as for example a photo detector.

The light source 2, 4, 6 and 8 is formed by a point source. Herefore, use is made of a small light bulb, for example a bicycle lamp. Since use is made of shadow images, the light source does not have to meet high requirements and simple means can be sufficient.

It is also possible to use a flash light. The latter offers the advantage of illuminating shortly while realizing, however, a sufficient light intensity to form a clear shadow image. Moreover, flash lights allow to switch quickly which shortens the measuring cycle time considerably and increases the efficiency of the device.

FIG. 2 shows the shadow image formation resulting from the method according to the invention. This example starts from the situation that lead 15 is illuminated by means of light source 2 and 4 respectively from a first and respectively a second position defined by a height $h_l$ and $h_r$ respectively and a distance $d_l$ and $d_r$ respectively with respect to the origin O of a coordinate system. Now, the height h (z-direction) and the distance d (x-direction) have to be determined in order to determine the position of lead 15. The y-coordinate is determined by using a measurement window as will be described hereinafter. The position is then determined three-dimensionally.

The light beam starting from light source 2 and 4 respectively will now form a first 17 and respectively a second 18 shadow image on the projection plane P which shadow image is situated on a third $x_l$ and respectively a fourth $x_r$ position. For simplicity's sake, the points $x_r$ and $x_l$ are each chosen in the middle of the shadow image but it would also be possible to choose another reference, such as for example a border line of the shadow image.

Determining the position of points $x_r$ and $x_l$ for locating the shadow images is realized now by determining the distance $x_r$ and $x_l$ respectively with respect to the origin O in the x-direction. This can be done for example by counting image points of the image recorded by the camera or by means of a grey value determination. Since $h_l$, $h_r$, $d_l$ en $d_r$ are known, the distances h and d can be calculated by means of the following equations:

$$h = \frac{1}{\frac{d_1 - x_1}{h_1} - \frac{d_r - x_r}{h_r}} (x_r - x_1)$$

$$d = \frac{1}{1 - \frac{(d_1 - x_1)h_r}{(d_r - x_r)h_1}} \left( x_1 - \frac{(d_1 - x_1)h_r}{(d_r - x_r)h_1} x_r \right)$$

This calculation is executed for example by the data processing unit which controls also the switching on and off of the light source. When determining a position of lead, the data processing unit will switch the light sources thus successively on and off in order to determine each time a position of the shadow image formed by means of the light source which is switched on only for the measurement.

Figure 4:
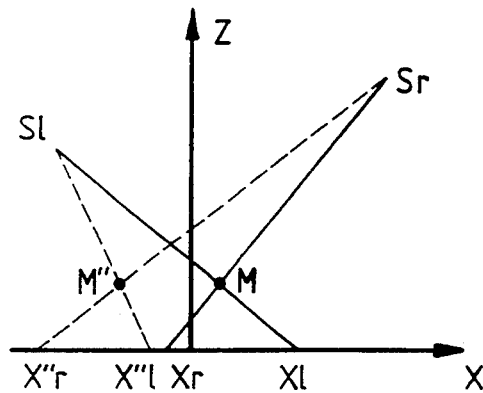
FIG. 4 shows the image formation for two different positions of a lead in a direction parallel to the projection plane.

The fact that different lead positions result also in different positions of the shadow images is illustrated by means of FIGS. 3 and 4. FIG. 3 illustrates the shadow images of a point M and M' the latter being shifted in the z-direction with respect to M. The shadow images of M' are situated on positions $x'_r$ and $x'_l$ which are clearly different from the positions $x_r$ and $x_l$. The same goes for the shadow images on the positions $x''_r$ and $x''_l$ formed by an element in position M'' as represented in FIG. 4 wherein position M'' is shifted in the x-direction with respect to M. Therefore, it results clearly from FIGS. 3 and 4 that each set of shadow images corresponds clearly to one lead position. The position of the lead can therefore be determined unambiguously and accurately from these shadow images.

In the embodiment shown in FIG. 2, the height h is determined with respect to the projection plane which coincides with the X-axis. However, the height h can be determined with respect to any other reference plane such as for example the plane formed by the bottom surface of the electronic component. However, in the latter case it is moreover necessary to determine first the position of this reference plane which can be realised also by means of shadow images as described hereinbefore.

Figure 5:
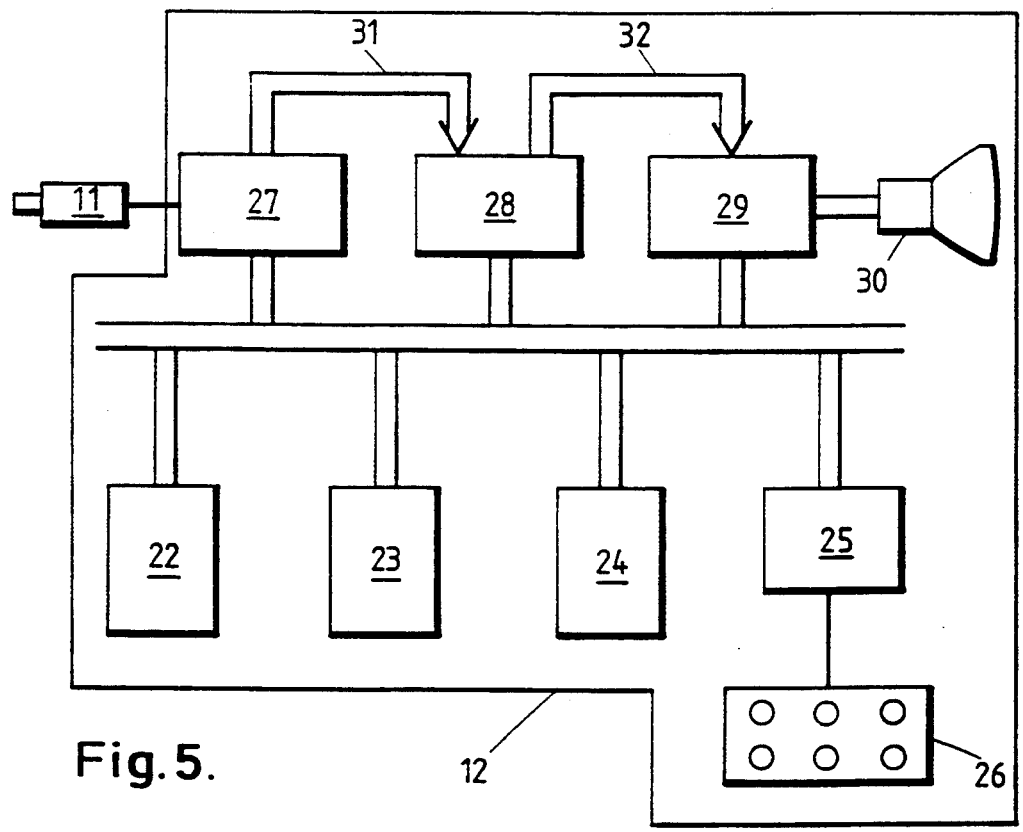
FIG. 5 shows a block diagram of data processing means to be used in a device according to the invention.

FIG. 5 shows an embodiment of the data processing unit 12 provided for controlling the device and for calculating the positions on the basis of the measured $x_r$ and $x_l$ values. The data processing unit comprises a communication bus 21, for example a VME busy and a microprocessor 22 and a first 23 and a second 24 memory connected to said bus. The first and respectively the second memory are for example a ROM and respectively a RAM. Further, an input-output interface 25 is connected to the bus 21. To the input-output interface is connected a control member 26 for controlling the device. Moreover, a sensor interface 27, an image fetching member 28 and a video generator 29 are connected to the bus 21. The latter elements are mutually connected by means of further busses 31 and 32, for example SC busses. The sensor interface is connected to the camera 11 while the video generator is connected to a display unit 30, for example a CRT.

The image formed by the camera 11 is scanned by the sensor interface 27 and converted into a digital image which is stored in a memory of the interface 27. The fetching member 28 fetches the image data out of the memory and processes them, for example by means of measuring windows to be defined in the formed image. Then the video generator makes an image of the image data, which image is represented on the screen of the display unit. The data processing is carried out under the control of the micro-processor 22 by means of programs stored in the ROM 23.

For determining the position of each lead of the electronic component, a window is defined around each lead. Herefore, use is made of the distance between the successive leads which is known per se. On the basis of the position of the window in the image as formed by the camera, an expected value is determined each time in order to delimit the area in which the shadow images are situated. This simplifies the search for the position of the shadow images. When determining the window, the length of the lead is taken into account.

When a window is defined around each of the leads to be considered, two profiles are determined for each window, i.e. a lead profile and a gravity profile. The lead profile is determined in the direction of the lead and represents the position of the individual leads. The gravity profile is determined across the lead and represents the middle of the leads.

After determining the lead profile, the grey value of each lead profile is compared to the one of a standard lead profile which is preferably triangular and which is obtained by taking a calibrating width (Ti) expressed as a number of image points and by choosing a height which gives the ratio between the height of the lead and the height of the window. The use of such triangular standard profiles offers the advantage of keeping the tolerances low. Then, the center of the lead is calculated from this lead profile in a way known per se. Afterwards, the X- and respectively Y-positions of the horizontal and respectively vertical series of leads are calculated from the mean value of these individual lead positions.

By using the gravity profile, the position of the horizontal and respectively vertical series of leads in the Y-and respectively X-direction are determined by calculating the gravity centers for each lead.

These calculations are all carried out by using the data processing system with its corresponding programs.

What is claimed is:

1. A method for determining, with respect to a reference plane, a position of at least one lead of an electronic component, said method comprising:
   illuminating said lead from a first position situated sideways and out of a component plane defined by said electronic component and thereby forming within an image plane a first shadow image of at least a part of said lead;
   determining within said image plane coordinates of a first location of at least a first predetermined point situated within said first shadow image;
   illuminating said lead from a second position different from said first position and situated sideways and out of said component plane and thereby forming within said image plane a second shadow image of at least a part of said lead;
   determining within said image plane coordinates of a second location of at least a second predetermined point situated within said second shadow image; and
   determining said position of said lead from said coordinates of said first and second location.

2. A method according to claim 1 wherein said first and respectively second point is located substantially in the middle of said first and respectively second shadow image.

3. A method according to claim 1 wherein illuminating from said first and second position is done from substantially opposite positions.

4. A method according to claim 1 wherein a further predetermined point is selected within said reference plane, said further predetermined point being illuminated from said first position thereby forming within said image plane a first reference point shadow image, said method further comprising:

determining within said image plane coordinates of a first reference location situated within said first reference shadow image;

illuminating said further predetermined point from said second position, thereby forming within said image plane a second reference point shadow image;

determining within said image plane coordinates of a second reference location situated within said second reference shadow image; and determining said position of said further predetermined point coordinates of said first and second reference locations.

5. A method for determining, with respect to a reference plane, a position of at least one lead of a semi-conductive element, said method comprising:

illuminating said lead from a first position situated sideways and out of a component plane defined by said semi-conductive element and thereby forming within an image plane a first shadow image of at least a part of said lead;

determining within said image plane coordinates of a first location of at least a first predetermined point situated within said first shadow image;

illuminating said lead from a second position different from said first position and situated sideways and out of said component plane and thereby forming within said image plane a second shadow image of at least a part of said lead;

determining within said image plane coordinates of a second location of at least a second predetermined point situated within said second shadow image; and determining said position of said lead from said coordinates of said first and second location.

6. A method according to claim 5 wherein said first and respectively second point is located substantially in the middle of said first and respectively second shadow image.

7. A method according to claim 5 wherein illuminating from said first and second position is done from substantially opposite positions.

8. A method according to claim 5 wherein a further predetermined point is selected within said reference plane, said further predetermined point being illuminated from said first position thereby forming within said image plane a first reference point shadow image, said method further comprising:

determining within said image plane coordinates of a first reference location situated within said first reference shadow image;

illuminating said further predetermined point from said second position, thereby forming within said image plane a second reference point shadow image;

determining within said image plane coordinates of a second reference location situated within said second reference shadow image; and determining said position of said further predetermined point coordinates of said first and second reference locations.

9. A device for determining, with respect to a reference plane, a position of at least one lead of an electronic component, said device comprising:

illumination means provided for illuminating said lead from a first and respectively a second position situated sideways and out of a component plane defined by said electronic component, said first and second position being different from each other;

an image formation member provided for forming within an image plane a first and respectively a second shadow image of at least a part of said lead upon illumination of said lead from said first and respectively said second position;

a position determining member cooperating with said image formation member and provided for determining, within said image plane, coordinates of a first and respectively a second location of at least a first and respectively a second predetermined point situated within said first and respectively said second shadow image and for further determining said position of said lead from said coordinates of said first and second location.

10. A device according to claim 9 wherein said illumination means comprise a first and respectively a second light source disposed in said first and respectively second position.

11. A device according to claim 10, wherein each said light source is a point source.

12. A device according to claim 11 wherein said point source is formed by a bicycle lamp.

13. A device according to claim 9 wherein said first and second position are situated substantially opposite to each other.

14. A device according to claim 9 wherein said position determining member is provided for determining said position from the difference between said coordinates of said first and said second location.

15. A device according to claim 9 wherein said device comprises a frosted-glass plate disposed in a beam path extending between said lead and said image formation member.

16. A device according to claim 9 wherein said image formation member comprises a camera.

* * * * *